US005552381A

United States Patent [19]

Atkinson

[11] Patent Number: 5,552,381

[45] Date of Patent: Sep. 3, 1996

[54] RECOMBINANTLY PRODUCED HUMAN MEMBRANE COFACTOR PROTEIN (MCP) PHARMACEUTICAL COMPOSITION, AND METHOD OF INHIBITING COMPLEMENT ACTIVITY

[75] Inventor: John P. Atkinson, St. Louis, Mo.

[73] Assignee: Washington University, St. Louis, Mo.

[21] Appl. No.: 203,867

[22] Filed: Feb. 28, 1994

Related U.S. Application Data

[63] Continuation of Ser. No. 984,247, Nov. 30, 1992, abandoned, which is a continuation of Ser. No. 510,709, Apr. 19, 1990, abandoned, which is a continuation-in-part of Ser. No. 384,210, Jul. 21, 1989, abandoned.

[51] Int. Cl.[6] ........................ A61K 38/17; C07K 14/435; C07K 14/705

[52] U.S. Cl. ................................ 514/8; 514/12; 530/350; 530/395; 530/380; 530/829; 435/69.1

[58] Field of Search ................................ 435/69.1, 70.1; 514/8, 12; 530/350, 380, 395, 829

[56] References Cited

U.S. PATENT DOCUMENTS

| | | | |
|---|---|---|---|
| 5,135,916 | 8/1992 | Sims et al. | 530/380 |
| 5,159,063 | 10/1992 | Hammer et al. | 530/380 |
| 5,179,198 | 1/1993 | Okada et al. | 530/395 |

FOREIGN PATENT DOCUMENTS

| | | | |
|---|---|---|---|
| 8901041 | 2/1989 | WIPO | C12N 15/00 |

OTHER PUBLICATIONS

Birmingham et al, J. Immunol. 142:3140–3144 (May 1989).
Seya, *Hok. Igaku Zasshi* 63:259–268 (Mar. 1988).
Seya et al, *Biochem. J.* 264:581–588 (Dec. 1989).
Hara et al, *Clin. Exp. Immunol.* 89:490–494 (Sep. 1992).
Stites et al, *Basic And Clinical Immunology*, pp. 136, 137, 410 (1991).
Holers et al., *Immunol. Today* (1985) 6(6):188–192.
Ross et al., *Adv. Immunol.* (1985) 37:217–267.
Atkinson et al., *Immunol. Today* (1987) 8(7&8):212–215.
Cole et al., *Proc. Natl. Acad. Sci.* (1985) 82:859–863.
Seya et al., *J. Exp. Med.* (1986) 163:837–855.
Ballard et al., *J. Immunol.* (1987) 138(11):3850–3855.
Seya et al., *Eur. J. Immunol.* (1988) 18:1289–1294.
Lublin et al., *Ann. Rev. Immunol.* (1989) 7:35–58.
McNearney et al., *J. Clin. Invest.* (1989) 84:001–008.
Lublin et al., *Current Topics in Microbiology and Immunology* J. D. Lambris, ed., (1989) 153:123–145.
Medof et al., *Proc. Natl. Acad. Sci.* (1987) 84:2007–2011.
Caras et al., *Nature* (1987) 325:545–549.
Goujet–Zalc et al., *Cellular Immunol.* (1987) 109:282–294.
Wong et al., *J. Immunol.* (1985) 134:4048–4056.
Schneider et al., *J. Immunol.* (1981) 290:789–792.
Cui et al., *FASEB Journal* (1989) 3:A500, Number 1594.
Yu et al., *J. Clin. Invest.* (1986) 78:494–501.
Caras et al., *Science* (1987) 238:1280–1283.
Seya et al., *Complement* (1987) 4:255.
Lublin et al., *J. Exp. Med.* (1987) 165:1731–1736.
Lublin et al., *J. Exp. Med.* (1988) 168:181–194.
Ballard et al., *J. Immunol.* (1988) 141(11):3923–3929.
Seya et al., *Biochem. J.* (1989) 264:581–588.
Stafford et al., Proc. *Natl. Acad. Sci. USA* (1988) 85:880–884.
Bora et al., *J. Exp. Med.* (1989) 169:597–602.
Farries et al., *Complement & Inflammation* (1990) 7:30–41.
Hourcade et al. *Progress in Immunology* (1989) VII:171–177.
Reid et al., *Immunol. Today* (1986) 7(7&8):230–234.
Purcell et al., *Immunology* (1990) 70:155–161.
Kim, *J. Biol. Chem.* (1989) 264(17):9780–9784.
Hourcade et al., Adv. Immunol. (1989) 45:381–416.

*Primary Examiner*—Stephen G. Walsh
*Attorney, Agent, or Firm*—Arnall Golden & Gregory

[57] ABSTRACT

Human membrane cofactor protein (MCP), a protein involved in regulation of complement activity, has been purified to homogeneity. The cDNAs encoding six isoforms of this protein have been retrieved and permit deduction of the complete amino acid sequences and the recombinant production of proteins with this activity. Pharmaceutical compositions in which MCP is the active ingredient for use in treating autoimmune diseases, antibody preparations for diagnosis, and DNA probes are also disclosed.

14 Claims, 17 Drawing Sheets

FIG. 1-1

```
TCTGCTTTCCTCCGGAGAAATAACAGCGTCTTCCGCGCCGCGCATGGAGCCTCCCGGCCGCCGCGAGTGTCCC  73
                                             M  E  P  P  G  R  R  E  C  P    25
                                            -34

TTTCCTTCCTGGCGCTTTCCTGGGTTGCTTCTGGCGGCCATGGTGTTGCTGCTGTACTCCTTCTCCGATGCC  145
 F  P  S  W  R  F  P  G  L  L  L  A  A  M  V  L  L  L  Y  S  F  S  D  A     1
                                                                       -1

TGTGAGGAGCCACCAACATTTGAAGCTATGGAGCTCATTGGTAAACCAAAACCCTACTATGAGATTGGTGAA  217
 C  E  E  P  P  T  F  E  A  M  E  L  I  G  K  P  K  P  Y  Y  E  I  G  E    24
+1

CGAGTAGATTATAAGTGTAAAAAAGGATACTTCTATATACCTCCTCTTGCCACCCATACTATTTGTGATCGG  289
 R  V  D  Y  K  C  K  K  G  Y  F  Y  I  P  P  L  A  T  H  T  I  C  D  R    48

AATCATACATGGCTACCTGTCTCAGATGACGCCTGTTATAGAGAAACATGTCCATATATACGGGATCCTTTA  361
 N  H  T  W  L  P  V  S  D  D  A  C  Y  R  E  T  C  P  Y  I  R  D  P  L    72
 ▲

AATGGCCAAGCAGTCCCTGCAAATGGGACTTACGAGTTTGGTTATCAGATGCACTTTATTTGTAATGAGGGT  433
 N  G  Q  A  V  P  A  N  G  T  Y  E  F  G  Y  Q  M  H  F  I  C  N  E  G    96
                      ▲

TATTACTTAATTGGTGAAGAAATTCTATATTGTGAACTTAAAGGATCAGTAGCAATTTGGAGCGGTAAGCCC  505
 Y  Y  L  I  G  E  E  I  L  Y  C  E  L  K  G  S  V  A  I  W  S  G  K  P   120

CCAATATGTGAAAAGGTTTTGTGTACACCACCTCCAAAAATAAAAAATGGAAAACACACCTTTAGTGAAGTA  577
 P  I  C  E  K  V  L  C  T  P  P  P  K  I  K  N  G  K  H  T  F  S  E  V   144

GAAGTATTTGAGTATCTTGATGCAGTAACTTATAGTTGTGATCCTGCACCTGGACCAGATCCATTTTCACTT  649
 E  V  F  E  Y  L  D  A  V  T  Y  S  C  D  P  A  P  G  P  D  P  F  S  L   168
```

FIG. 1-2

```
ATTGGAGAGAGCACGATTTATTGTGGTGACAATTCAGTGTGGAGTCGTGCTGCTCCAGAGTGTAAAGTGGTC  721
 I  G  E  S  T  I  Y  C  G  D  N  S  V  W  S  R  A  A  P  E  C  K  V  V   192

AAATGTCGATTTCCAGTAGTCGAAAATGGAAAACAGATATCAGGATTTGGAAAAAAATTTTACTACAAAGCA  793
 K  C  R  F  P  V  V  E  N  G  K  Q  I  S  G  F  G  K  K  F  Y  Y  K  A   216

ACAGTTATGTTTGAATGCGATAAGGGTTTTTACCTCGATGGCAGCGACACAATTGTCTGTGACAGTAACAGT  865
 T  V  M  F  E  C  D  K  G  F  Y  L  D  G  S  D  T  I  V  C  D  S  N  S   240
                                                                     ▲

ACTTGGGATCCCCCAGTTCCAAAGTGTCTTAAAGTGTCGACTTCTTCCACTACAAAATCTCCAGCGTCCAGT  937
 T  W  D  P  P  V  P  K  C  L  K  V  S  T  S  S  T  T  K  S  P  A  S  S   264

GCCTCAGGTCCTAGGCCTACTTACAAGCCTCCAGTCTCAAATTATCCAGGATATCCTAAACCTGAGGAAGGA 1009
 A  S  G  P  R  P  T  Y  K  P  P  V  S  N  Y  P  G  Y  P  K  P  E  E  G   288

ATACTTGACAGTTTGGATGTTTGGGTCATTGCTGTGATTGTTATTGCCATAGTTGTTGGAGTTGCAGTAATT 1081
 I  L  D  S  L  D  V  W  V  I  A  V  I  V  I  A  I  V  V  G  V  A  V  I   312

TGTGTTGTCCCGTACAGATATCTTCAAAGGAGGAAGAAGAAAGGGAAAGCAGATGGTGGAGCTGAATATGCC 1153
 C  V  V  P  Y  R  Y  L  Q  R  R  K  K  K  G  K  A  D  G  G  A  E  Y  A   336

ACTTACCAGACTAAATCAACCACTCCAGCAGAGCAGAGAGGCTGAATAGATTCCACAACCTGGTTTGCCAGT 1225
 T  Y  Q  T  K  S  T  T  P  A  E  Q  R  G  *                              350

TCATCTTTTGACTCTATTAAAATCTTCAATAGTTGTTATTCTGTAGTTTCACTCTCATGAGTGCAACTGTGG 1297
```

```
CTTAGCTAATATTGCAATGTGGCTTGAATGTAGGTAGCATCCTTTGATGCTTCTTTGAAACTTGTATGAATT 1369

TGGGTATGAACAGATTGCCTGCTTTCCCTTAAATAACACTTAGATTTATTGGACCAGTCAGCACAGCATGCC 1441

TGGTTGTATTAAAGCAGGGATATGCTGTATTTTATAAAATTGGCAAAATTAGAGAAATATAGTTCACAATGA 1513

AATTATATTTTCTTTGTAAAAAAAAAAAAAAAA                                        1546
```

```
         10        20        30        40        50        60
GCCCACCTGTCCTGCAGCACTGGATGCTTTGTGAGTTGGGGATTGTTGCGTCCCATATCT

         70        80        90       100       110       120
GGACCCAGAAGGGACTTCCCTGCTCGGCTGGCTCTCGGTTTCTCTGCTTTCCTCCGGAGA

        130       140       150       160       170       180
AATAACAGCGTCTTCCGCGCCGCGCATGGAGCCTCCCGGCCGCCGCGAGTGTCCCTTTCC
                         M  E  P  P  G  R  R  E  C  P  F  P

        190       200       210       220       230       240
TTCCTGGCGCTTTCCTGGGTTGCTTCTGGCGGCCATGGTGTTGCTGCTGTACTCCTTCTC
 S  W  R  F  P  G  L  L  L  A  A  M  V  L  L  L  Y  S  F  S

        250       260       270       280       290       300
CGATGCCTGTGAGGAGCCACCAACATTTGAAGCTATGGAGCTCATTGGTAAACCAAAACC
 D  A  C  E  E  P  P  T  F  E  A  M  E  L  I  G  K  P  K  P

        310       320       330       340       350       360
CTACTATGAGATTGGTGAACGAGTAGATTATAAGTGTAAAAAAGGATACTTCTATATACC
 Y  Y  E  I  G  E  R  V  D  Y  K  C  K  K  G  Y  F  Y  I  P

        370       380       390       400       410       420
TCCTCTTGCCACCCATACTATTTGTGATCGGAATCATACATGGCTACCTGTCTCAGATGA
 P  L  A  T  H  T  I  C  D  R  N  H  T  W  L  P  V  S  D  D
```

FIG.2-2

```
        430        440        450        460        470        480
CGCCTGTTATAGAGAAACATGTCCATATATACGGGATCCTTTAAATGGCCAAGCAGTCCC
 A  C  Y  R  E  T  C  P  Y  I  R  D  P  L  N  G  Q  A  V  P

        490        500        510        520        530        540
TGCAAATGGGACTTACGAGTTTGGTTATCAGATGCACTTTATTTGTAATGAGGGTTATTA
 A  N  G  T  Y  E  F  G  Y  Q  M  H  F  I  C  N  E  G  Y  Y

        550        560        570        580        590        600
CTTAATTGGTGAAGAAATTCTATATTGTGAACTTAAAGGATCAGTAGCAATTTGGAGCGG
 L  I  G  E  E  I  L  Y  C  E  L  K  G  S  V  A  I  W  S  G

        610        620        630        640        650        660
TAAGCCCCCAATATGTGAAAAGGTTTTGTGTACACCACCTCCAAAAATAAAAAATGGAAA
 K  P  P  I  C  E  K  V  L  C  T  P  P  P  K  I  K  N  G  K

        670        680        690        700        710        720
ACACACCTTTAGTGAAGTAGAAGTATTTGAGTATCTTGATGCAGTAACTTATAGTTGTGA
 H  T  F  S  E  V  E  V  F  E  Y  L  D  A  V  T  Y  S  C  D

        730        740        750        760        770        780
TCCTGCACCTGGACCAGATCCATTTTCACTTATTGGAGAGAGCACGATTTATTGTGGTGA
 P  A  P  G  P  D  P  F  S  L  I  G  E  S  T  I  Y  C  G  D

        790        800        810        820        830        840
CAATTCAGTGTGGAGTCGTGCTGCTCCAGAGTGTAAAGTGGTCAAATGTCGATTTCCAGT
 N  S  V  W  S  R  A  A  P  E  C  K  V  V  K  C  R  F  P  V

        850        860        870        880        890        900
AGTCGAAAATGGAAAACAGATATCAGGATTTGGAAAAAAATTTTACTACAAAGCAACAGT
 V  E  N  G  K  Q  I  S  G  F  G  K  K  F  Y  Y  K  A  T  V
```

FIG.2-3

```
      910       920       930       940       950       960
TATGTTTGAATGCGATAAGGGTTTTTACCTCGATGGCAGCGACACAATTGTCTGTGACAG
 M  F  E  C  D  K  G  F  Y  L  D  G  S  D  T  I  V  C  D  S

      970       980       990      1000      1010      1020
TAACAGTACTTGGGATCCCCCAGTTCCAAAGTGTCTTAAAGTGTCGACTTCTTCCACTAC
 N  S  T  W  D  P  P  V  P  K  C  L  K  V  S  T  S  S  T  T

     1030      1040      1050      1060      1070      1080
AAAATCTCCAGCGTCCAGTGCCTCAGGTCCTAGGCCTACTTACAAGCCTCCAGTCTCAAA
 K  S  P  A  S  S  A  S  G  P  R  P  T  Y  K  P  P  V  S  N

     1090      1100      1110      1120      1130      1140
TTATCCAGGATATCCTAAACCTGAGGAAGGAATACTTGACAGTTTGGATGTTTGGGTCAT
 Y  P  G  Y  P  K  P  E  E  G  I  L  D  S  L  D  V  W  V  I

     1150      1160      1170      1180      1190      1200
TGCTGTGATTGTTATTGCCATAGTTGTTGGAGTTGCAGTAATTTGTGTTGTCCCGTACAG
 A  V  I  V  I  A  I  V  V  G  V  A  V  I  C  V  V  P  Y  R

     1210      1220      1230      1240      1250      1260
ATATCTTCAAAGGAGGAAGAAGAAAGGAAAGCAGATGGTGGAGCTGAATATGCCACTTA
 Y  L  Q  R  R  K  K  K  G  K  A  D  G  G  A  E  Y  A  T  Y

     1270      1280      1290      1300      1310      1320
CCAGACTAAATCAACCACTCCAGCAGAGCAGAGAGGCTGAATAGATTCCACAACCTGGTT
 Q  T  K  S  T  T  P  A  E  Q  R  G  U

     1330      1340      1350      1360      1370      1380
TGCCAGTTCATCTTTTGACTCTATTAAAATCTTCAATAGTTGTTATTCTGTAGTTTCACT
```

FIG.2-4

```
           1390        1400        1410        1420        1430        1440
CTCATGAGTGCAACTGTGGCTTAGCTAATATTGCAATGTGGCTTGAATGTAGGTAGCATC

           1450        1460        1470        1480        1490        1500
CTTTGATGCTTCTTTGAAACTTGTATGAATTTGGGTATGAACAGATTGCCTGCTTTCCCT

           1510        1520        1530        1540        1550        1560
TAAATAACACTTAGATTTATTGGACCAGTCAGCACAGCATGCCTGGTTGTATTAAAGCAG

           1570        1580        1590        1600        1610        1620
GGATATGCTGTATTTTATAAAATTGGCAAAATTAGAGAAATATAGTTCACAATGAAATTA

           1630        1640        1650        1660        1670        1680
TATTTTCTTTGTAAAGAAAGTGGCTTGAAATCTTTTTTGTTCAAAGATTAATGCCAACTC

           1690        1700        1710        1720        1730        1740
TTAAGATTATTCTTTCACCAACTATAGAATGTATTTTATATATCGTTCATTGTAAAAAGC

           1750        1760        1770        1780        1790        1800
CCTTAAAAATATGTGTATACTACTTTGGCTCTTGTGCATAAAAACAAGAACACTGAAAAT

           1810        1820        1830        1840        1850        1860
TGGGAATATGCACAAACTTGGCTTCTTTAACCAAGAATATTATTGGAAAATTCTCTAAAA

           1870        1880        1890        1900        1910        1920
GTTAATAGGGTAAATTCTCTATTTTTTGTAATGTGTTCGGTGATTTCAGAAAGCTAGAAA

           1930        1940        1950        1960        1970        1980
GTGTATGTGTGGCATTTGTTTTCACTTTTTAAAACATCCCTAACTGATCGAATATATCAG

           1990        2000        2010        2020        2030        2040
TAATTTCAGAATCAGATGCATCCTTTCATAAGAAGTGAGAGGACTCTGACAGCCATAACA
```

FIG.2-5

```
      2050       2060       2070       2080       2090       2100
GGAGTGCCACTTCATGGTGCGAAGTGAACACTGTAGTCTTGTTGTTTTCCCAAAGAGAAC

      2110       2120       2130       2140       2150       2160
TCCGTATGTTCTCTTAGGTTGAGTAACCCACTCTGAATTCTGGTTACATGTGTTTTTCTC

      2170       2180       2190       2200       2210       2220
TCCCTCCTTAAATAAAGAGAGGGGTTAAACATGCCCTCTAAAAGTAGGTGGTTTTGAAGA

      2230       2240       2250       2260       2270       2280
GAATAAATTCATCAGATAACCTCAAGTCACATGAGAATCTTAGTCCATTTACATTGCCTT

      2290       2300       2310       2320       2330       2340
GGCTAGTAAAAGCCATCTATGTATATGTCTTACCTCATCTCCTAAAAGGCAGAGTACAAA

      2350       2360       2370       2380       2390       2400
GTAAGCCATGTATCTCAGGAAGGTAACTTCATTTTGTCTATTTGCTGTTGATTGTACCAA

      2410       2420       2430       2440       2450       2460
GGGATGGAAGAAGTAAATATAGCTCAGGTAGCACTTTATACTCAGGCAGATCTCAGCCCT

      2470       2480       2490       2500       2510       2520
CTACTGAGTCCCTTAGCCAAGCAGTTTCTTTCAAAGAAGCCAGCAGGCGAAAAGCAGGGA

      2530       2540       2550       2560       2570       2580
CTGCCACTGCATTTCATATCACACTGTTAAAAGTTGTGTTTTGAAATTTTATGTTTAGTT

      2590       2600       2610       2620       2630       2640
GCACAAATTGGGCCAAAGAAACATTGCCTTGAGGAAGATATGATTGGAAAATCAAGAGTG

      2650       2660       2670       2680       2690       2700
TAGAAGAATAAATACTGTTTTACTGTCCAAAGACATGTTTATAGTGCTCTGTAAATGTTC
```

FIG.2-6

```
        2710      2720      2730      2740      2750      2760
CTTTCCTTTGTAGTCTCTGGCAAGATGCTTTAGGAAGATAAAAGTTTGAGGAGAACAAAC

        2770      2780      2790      2800      2810      2820
AGGAATTCTGAATTAAGCACAGAGTTGAAGTTTATACCCGTTTCACATGCTTTTCAAGAA

        2830      2840      2850      2860      2870      2880
TGTCGCAATTACTAAGAAGCAGATAATGGTGTTTTTAGAAACCTAATTGAAGTATATTC

        2890      2900      2910      2920      2930      2940
AACCAAATACTTTAATGTATAAAATAAATATTATACAATATACTTGTATAGCAGTTTCTG

        2950      2960      2970      2980      2990      3000
CTTCACATTTGATTTTTTCAAATTTAATATTTATATTAGAGATCTATATATGTATAAATA

        3010      3020      3030      3040      3050      3060
TGTATTTTGTCAAATTTGTTACTTAAATATATAGAGACCAGTTTTCTCTGGAAGTTTGTT

        3070      3080      3090      3100      3110      3120
TAAATGACAGAAGCGTATATGAATTCAAGAAAATTTAAGCTGCAAAAATGTATTTGCTAT

        3130      3140      3150      3160      3170      3180
AAAATGAGAAGTCTCACTGATAGAGGTTCTTTATTGCTCATTTTTTAAAAAATGGACTCT

        3190      3200      3210      3220
TGAAATCTGTTAAAATAAAATTGTACATTTGGAAAAAAAAAAAA
```

CYT[1]

1 ... 70

CACATACCTAACTGATGAGACCCACAGAGAAGTAAAATTTACTTCTCTCTGAGAAGGAGAGATGAGAGAAAGGTTTGCTTTTATCATTAAAAG

T Y L T D E T H R E V K F T S L U

ST[A]

TGCTGCCTCCATCTAGTACAAAACCTCCAGCTTTGAGTCATTCAG

Exon/Intron Junctions

| Exon | Protein Domain | 5′Intron | Exon | | | | 3′Intron | Exon Size (bp) |
|---|---|---|---|---|---|---|---|---|
| 1 | 5′UT/SP | — | | | .......TCC | G | gtagg | - |
| 2 | SCR I | cctag | AT | GCC...TAT | | A | gtaag | 189 |
| 3 | SCR IIA | ttcag | GA | GAA...GAG | | GG | gtaag | 103 |
| 4 | SCR IIB | tttag | T | TAT...GAA | | A | gtaag | 86 |
| 5 | SCR III | tttag | AG | GTT...AAA | | G | gtagt | 198 |
| 6 | SCR IV | tccag | TG | GTC...AAA | | G | gtaca | 183 |
| 7 | $ST^A$ | cctag | TG | CTG...TCA | | G | gttta | 45 |
| 8 | $ST^B$ | tccag | TG | TCG...TCA | | G | gttta | 45 |
| 9 | $ST^C$ | tctag | GT | CCT...CCA | | G | gttgg | 42 |
| 10 | UK | cctag | GA | TAT...TTG | | G | gttgg | 39 |
| 11 | $HY^1$ | ctcag | AT | GTT...ATA | | G | gtaag | 55 |
| 12 | $HY^2$ | tatag | TT | GTT...AAA | | GG | gtaaa | 64 |
| 13 | $CYT^1$ | tatag | C | ACA...AAA | | AG | gtaaa | 93 |
| 14 | $CYT^2$/3′UT | tgcag | G. | AAA...... | | | — | 1985 |

```
      C E E P P T F E A M E L I G K P K P - - - - Y Y E I G E R V D Y K C K K - - G   1- 33
R E T C - - P - Y I R - D P L N G Q A V P A N G T - Y E F G Y Q M H F I C N E - - G  62- 96
K V L C T P P P K I K - - - - - N G K H T F S E V E V F E Y L D A V T Y S C D P A P G 125-162
V V K C R F P - V V E - - - - - N G K Q I S G F G K K F Y Y K A T V M F E C D K - - G 191-225

      C     P     L                                                   F   C         G
                  I                                                   Y
                  V

- - Y F Y I P P L A T H T I - C - D R N H T - - - W L P V S D D A C Y  34- 61
- - - Y Y L I G E E I - - L Y C - E L K G S V A I W S G K - P P I C E  97-124
P D P F S L I G E S T - - I Y C G D - N - S V - - W S R A - A P E C K 163-190
- - - F Y L D G S D T - - I V C - D S N S T - - - W D P P - V P K C L 226-250

      F       G               C                   W             P   C
      Y
```

| 4SCRs | ST$^A$ | ST$^B$ | ST$^C$ | UK |
|---|---|---|---|---|
| 1–251 | VLPPSSTKPPALSHS | VSTSSTTKSPASSAS | GPRPTYKPPVSNYP | 281–294 |
| of Fig. 1 | | 252–266 | 267–280 | of Fig. 1 |
| | | of Fig. 1 | of Fig. 1 | |

| HY | CYT$^1$ |
|---|---|
| 295–326 | TYLTDETHREVKFTSL |
| of Fig. 1 | |

| CYT$^2$ |
|---|
| 327–350 |
| of Fig. 1 |

5′ Oligonucleotide - [MG16C(ER1)]

(Sal 1, Eco R1) ATTGTTGCGTCCCATATCTGGACCCAGAAGGG

3′ Oligonucleotide - [MG11N(ER1)]

(Sal 1, Eco R1) AAGCCACATTGCAATATTAGCTAAGCCACAGT

RECOMBINANTLY PRODUCED HUMAN MEMBRANE COFACTOR PROTEIN (MCP) PHARMACEUTICAL COMPOSITION, AND METHOD OF INHIBITING COMPLEMENT ACTIVITY

This is a continuation of U.S. Ser. No. 07/984,247 filed Nov. 30, 1992, now abandoned, which is a continuation of U.S. Ser. No. 07/510,709 filed Apr. 19, 1990, now abandoned which is a continuation in part of U.S. Ser. No. 07/384,210 filed Jul. 21, 1989, now abandoned.

TECHNICAL FIELD

The invention is related to human therapeutics and regulation of the complement cascade. More specifically, it concerns the recombinant production of human membrane cofactor protein (MCP) which is an important factor in the regulation of complement cascade.

BACKGROUND ART

The complement system is capable of tissue and cell destruction and is therefore a major element of the defense system against invasion by foreign tissue. However, control of this system is necessary in order to prevent destruction of autologous cells. A large number of proteins which are involved in control of the complement cascade have been described.

Most relevant to the present invention is the group which controls the C3 and C5 convertases of both the alternative and classical complement pathways. The target group thus includes serum proteins such as C4-binding protein and factor H and membrane proteins such as C3b receptor, C3d/Epstein-Barr virus receptor, decay-accelerating factor (DAF), and the protein of the invention, membrane factor protein (MRT). MTP inactivates both isolated C3b and C4b and the forms of these proteins as included in the convertases. Reviews of these various factors and their role in the complement cascade regulation can be found in Holers, V. M., et al., *Immunol Today* (1985) :6:188; Ross, G. D., et al., *Adv Immunol* (1985) 37:217; Atkinson, J. P., et al., *Immunol Today* (1987) 8:212; Hourcade, D., et al., *Adv Immunol* (1989) 45:381–416; Reid, K. B. M., et al., *Immunol Today* (1986) 7:230.

Much is known concerning these regulatory proteins, which are encoded at a single chromosomal location, the regulators of complement activation (RCA) cluster, except for MCP. They are each composed of multiple repeat of an approximately 60-amino acid consensus sequence composed of conserved cys, pro, gly, trp, leu/ile/val, and tyr/phe residues (Reid, K., et al., *Immunol Today* (1986) (supra). The genes encoding these proteins have been localized to the long arm of human chromosome 1, band lq32 and form the multigene family designated the RCA gene cluster. As will be shown below, MCP is also a member of this family.

The RCA encoded proteins regulate the complement pathways in two major ways—acceleration of the decay of the C3 convertases crucial to the pathway by reversible dissociation of their component proteins (decay accelerating function) and behavior as a cofactor in the irreversible factor I (a serine protease) mediated proteolytic deactivation of the convertase (cofactor activity), Hourcade, D., et al., *Adv Immunol* (supra).

A well-studied member of this family related to the MCP of the invention is the decay-accelerating factor (DAF), as recently reviewed by Lublin, D. M., et al., Ann *Rev Immunol*

(1989) 7:35–38. DAF is present on virtually all peripheral blood cells, including erythrocytes, granulocytes, T and B lymphocytes, monocytes, and platelets; in addition, soluble forms of DAF have been found in extracellular fluids and tissue culture supernatants. The gene encoding DAF has been cloned and sequenced by two groups: by Medof, M. E., et al., *Proc Natl Acad Sci USA* (1987) 84:2007–2011; and by Caras, I. W., et al., Nature (1987) 325:545–549. Two classes of DAF cDNAs have been found (Caras et al., Nature (supra)). The difference between the two forms is the addition of 118 bp near the carboxy terminus of one form; this insert resembles an Alu type of sequence and its internal boundaries match the intron consensus splice sequences. This has lead one group (Caras et al.) to postulate that this class of cDNAs include an unspliced, retained intron. The suggestion by Caras that the membrane and soluble secreted forms of DAF result from differential splicing of the mRNA to include an intron is also described in PCT application WO89/01041. It has been found by the inventors herein that the inserted sequence is encoded by exon 10 of the DAF gene, and that this exon is flanked by consensus splice junction sequences (Post et al., *J Immunol* (1990) 144:740). Therefore, the etiology of the two classes of DAF-encoding cDNAs is conventional alternative splicing of a distinct exon.

MCP was initially identified by iC3/C3b affinity chromatography on surface-labeled peripheral blood cells and designated gp45–70 to describe the range of $M_r$ obtained on SDS-PAGE (Cole, J. L., et al., *Proc Natl Acad Sci USA* (1985) 82:859). MCP was partially purified from the human mononuclear cell lines and shown to have a cofactor activity but no decay accelerating function (Seya, T. J., et al., *J Exp Med* (1986) 163:837). MCP is absent from erythrocytes, but present as a membrane-bound protein on human T and B lymphocytes, granulocytes, monocytes, platelets, endothelial cells, epithelial cells, and fibroblasts (Seya et al., *Eur J Immunol* (1988) 18:1289; McNearney, T., et al., *J Clin Invest* (1989) 84:538). The occurrence of MCP on a wide range of host cells is consistent with a role in protecting host cells from damage by complement (Hourcade, D., et al., *Adv Immunol* (supra); Lublin, D. L., and Atkinson, J. P., *Current Topic in Microbial and Immunol* (1989) 153:123–145). On most of these cells it occurs in two forms of molecular weight 63 kd and 68 kd, as determined by SDS-PAGE. The quantity of each of the two species expressed is under genetic control and involves a two allelic system (Ballard, L., et al., *J Immunol* (1987) 138:3850–3855). The MCP found by immunoprecipitation on the membranes of granulocytes appears, however, not to exhibit this polymorphism (Seya, T., et al., *Eur J Immunol* (1988) 18:1289–1294).

In addition to human MCP, MCP or MCP-like or MCP-related materials have been found in a variety of mammalian tissues. For example, a dimorphic protein of MW 65 kd and 69 kd is found on orangutan erythrocytes which binds to homologous C3, is immunoreactive with a monoclonal antibody raised against human MPC, and has cofactor activity, as described by Nickelis, M. W., et al., (1990) submitted. Both marmoset and rabbit also exhibit dimorphic proteins of 75 and 68 kd and of 55 and 45 kd from erythrocytes and platelets, respectively, which bind C3 (Goujet-Zalc, C., et al., *Cellular Immunol* (1987) 109:282; Manthei, U., et al., *J Immunol* (1988) 140:1228). In addition, erythrocytes of baboon, most cells in mice, and alveolar and peritoneal macrophages of rabbit produce a 65 kd protein which is capable to bind to C3 (Birmingham, D. J., et al., *J Immunol* (1989) 142:3140; Wong, W. W., et al., *J Immunol* (1985) 134:4048; Schneider, R. J., et al., *Nature* (1981) 190:789; Cui, W., et al., *FASEB Journal* (1989) 3:A500).

The previously purified human MCP has been utilized to prepare a polyclonal rabbit antiserum monospecific for this protein. The antisera were raised in rabbits by repetitive injections of MCP purified as described by Seya, T., et al., *J Exp Med* (1986) (supra), in complete Freund's adjuvant. These antisera have been used to identify MCP in extracts from various membranes.

The present invention provides a more highly purified form of this protein and the capacity to produce it recombinantly, thus providing practical quantities for therapeutic use. In addition, as shown hereinbelow, the MCP protein may be made recombinantly in a variety of forms with varying capacity for glycosylation and membrane binding, thus permitting regulation and optimization of therapeutic forms.

DISCLOSURE OF THE INVENTION

Membrane cofactor protein (MCP) of mammals is a significant protector of host tissue from autologous destruction by the complement system. Practical quantities of multiple isoforms of this protein and antibodies specifically immunoreactive with them are made available by the herein described recombinant production of MCP.

Accordingly, in one aspect, the invention is directed to purified and isolated mammalian, especially human, MCPs and to said MCPs produced recombinantly. In other aspects, the invention is directed to recombinant materials and methods which result in the manufacture of useful quantities of these proteins. Also an aspect of the invention are methods to diagnose disorders associated with reduced or elevated amounts of MCP using antibodies immunoreactive with individual MCP isoforms. Further, the invention includes DNA probes useful in detecting polymorphisms of the MCP-encoding gene, and in obtaining genomic or complementary DNA encoding corresponding MCP in other species or allelic variants in humans.

In still further aspects, the invention is directed to pharmaceutical compositions containing the MCP proteins of the invention and to methods of treating or ameliorating inflammatory and autoimmune conditions that are mediated by an excess or misdirection of complement activity.

In still another aspect, the invention is directed to methods to diagnose abnormalities in the immune system, specifically the presence or absence of autoimmune disease by assessing the levels of MCP present on peripheral blood cells and to a method to predict the probability of recurrent miscarriage by testing for levels of MCP in the placenta.

BRIEF DESCRIPTION OF THE DRAWINGS

FIGS. 1-1 to 1-3 show the nucleotide sequence of cDNA and deduced amino acid sequence of one isoform of human MCP having a $CYT^2$ C-terminus.

FIGS. 2-1 to 2-6 show the nucleotide sequence of cDNA and deduced amino acid sequence of the isoform of FIGS. 1-1 through 1-3 wherein the cDNA reflects an extended 3' untranslated region. FIG. 2-7 also shows the cDNA encoding $ST^a$ and $CYT^1$ and their deduced amino acid sequences.

FIG. 3 shows a diagrammatic representation of mRNAs encoding 6 different isoforms of human MCP.

FIG. 4 shows a diagrammatic representation of the genomic region encoding human MCP.

FIG. 5 shows the sequences at the exon/intron junctions for the genomic sequence of FIG. 4.

FIG. 6 shows the correspondence between the genomic exons and the various MCP isoforms.

FIG. 7 shows the correspondence of the four SCR sequences of human MCP.

MODES OF CARRYING OUT THE INVENTION

Figure 3:
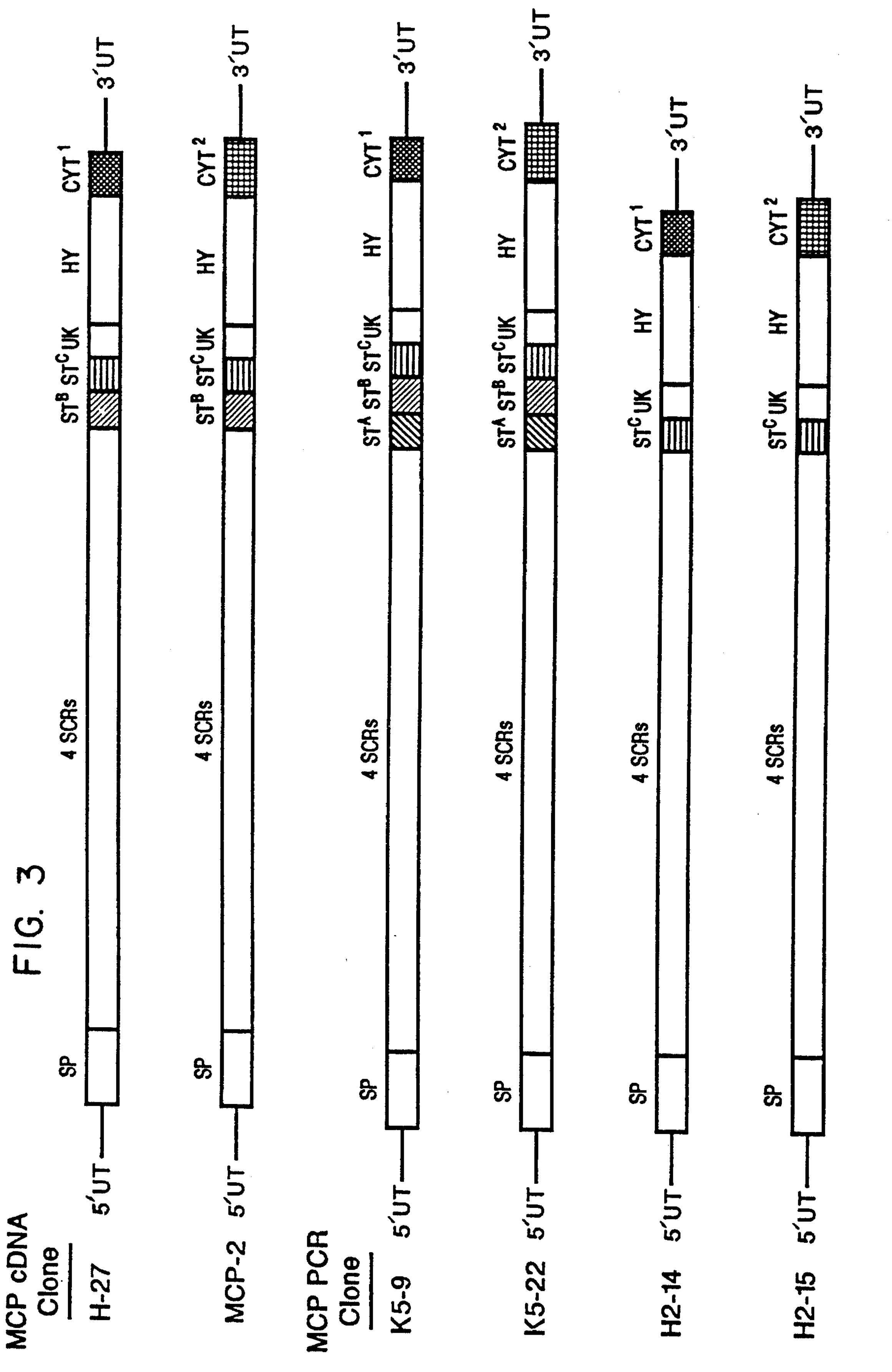

As used herein, "MCP" refers to proteins which show complement-inhibitory activity according to standard hemolysis assays described below, have cofactor activity according to the assay of Turner, J. R., et al., Masters Thesis, Washington U., St. Louis, Mo. (1984), incorporated herein by reference and are free of decay-accelerating function as assayed according to Hoffmann, E. M., *Immunochemistry* (1969) :6:405–419, incorporated herein by reference. Mammalian MCP refers to this protein referenced to any mammalian-derived protein in a manner analogous to that described for "human"MCP. "Human" MCP refers to proteins that have amino acid sequences referenced to that shown as one of the mature isoforms herein. By "referenced to" is meant that the protein contains the same amino acid sequence as that shown, is encoded by a DNA which represents an allelic variant of the DNA encoding the amino acid sequence shown, or has an amino acid sequence which has deletions, insertions, and/or substitutions of individual or multiple amino acid residues which do not alter the qualitative pattern of activity described. For example, and specifically included among amino acid sequences referenced to those of the isoforms, are those in which the membrane binding region (HY) is deleted, along with allelic variants of the remaining portion. The protein in soluble form is thus specifically included. This "soluble" form corresponds to any effective portion which does not contain the hydrophobic portion as described below. It is thus possible for the soluble MCP to be very short—containing only one or two of the short consensus repeats described below, with or without attached carbohydrate.

It should further be noted that solubilization of the MCP has an effect on its cofactor activity, which activity is variable depending on the conditions of the assay. This spectrum of activities is described in Seya, T., et al., *Biochem J* (1989) 264:581), also incorporated herein by reference. The results of the assays therein described showed that soluble MCP when added exogenously had only low activity as a cofactor for the cleavage of erythrocyte-bound C3b to iC3b or for the cleavage of C3b bound to zymosan. Conversely, cells bearing MCP were only weak cofactors for the cleavage by factor I of fluid phase C3b. However, exogenously added MCP and factor I gave efficient cleavage of erythrocyte-bound C3b if the concentration of detergent was made sufficient to solubilize the cells, or if C3b was attached to certain specified solubilized acceptor membrane molecules. Alternate solubilized acceptor membrane molecules bearing C3b were not as susceptible. The reaction of fluid phase and cell-bound 3Cb by soluble MCP and factor I produced i3Cb, but no C3c or C3dg.

In summary, soluble MCP has potent cofactor activity for fluid phase C3b or for C3b bound to solubilized molecules, but not to insoluble forms. Thus, it is to be expected that the power of the MCP protein as a cofactor will depend on the conditions of the assay in a manner described for naturally isolated MCP as is known, or as is studied in the art. Future work will determine whether MCP is an efficient cofactor for C3b bound to the same cell as MCP—i.e., endogenous MCP.

FIGS. 1-1 through 1-3 and 2-1 through 2-6 show the amino acid sequence for the human isoform of MCP for which cDNA was initially retrieved. These cDNAs differ only in the length of their untranslated regions. The 3' untranslated sequences are different, that of FIGS. 2-1 through 2-6 being considerably longer and utilizing the commonly found polyadenylation signal AATAAA, while the 3' untranslated region of FIGS. 1-1 through 1-3 utilize AATATA or AATGAA in a shorter (approximately 0.35 kb) sequence. FIG. 3, however, diagrams the mRNAs encoding six isoforms of the MCP protein for which cDNAs have been recovered. These isoforms differ in their capacity for glycosylation and in the nature of their cytoplasmic tail regions.

Figure 8:
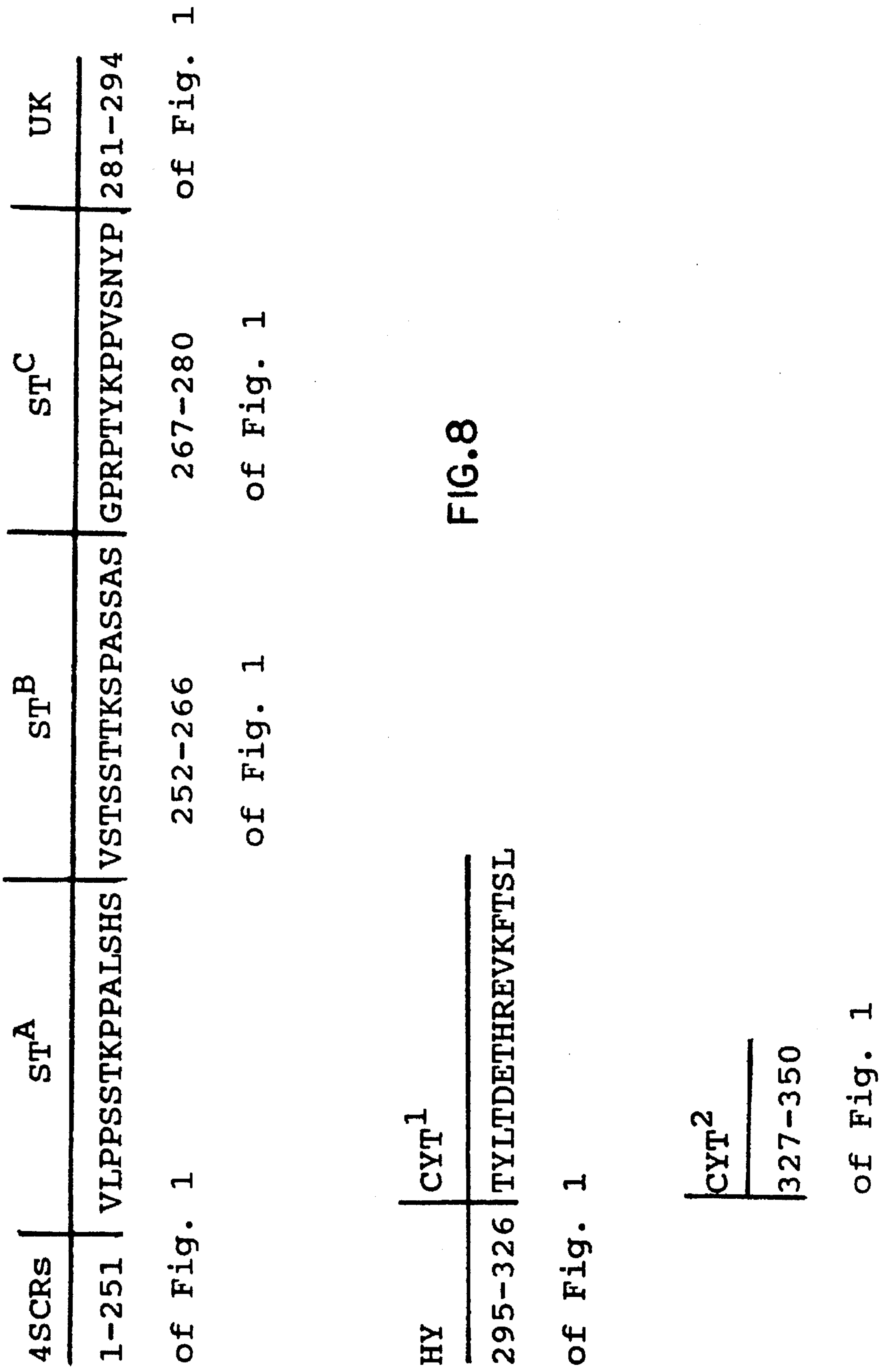
FIG. 8 shows the amino acid sequences for the various ST regions and the alternative CYT regions of six MCP isoforms.

As shown in FIG. 3, all of the human isoforms of MCP for which cDNA have been prepared share certain structural characteristics. In the messenger RNA diagramed, there is a 5' untranslated region followed by the coding sequence for a signal protein responsible for the carrying the mature MCP to the Golgi for binding to the membrane. This is followed by four short consensus repeat (SCR) sequences shared with the other proteins which are encoded by the RCA gene complex. These approximately 60 amino acid repeats have the sequences shown in FIGS. 1-1 through 1-3 and 2-1 through 2-6 between amino acids 1–251, and the nature of this consensus is shown in detail in FIG. 7. The series of four SCRs is shared by all of the isoforms, and is followed by at least one serine-threonine rich region (ST region) in all of the retrieved isoforms. As is evident in FIG. 3, two of the isoforms contain only the $ST^c$ serine-threonine rich region; two of them contain both $ST^b$ and $ST^c$ and two of them contain $ST^a$ $ST^b$ and $ST^c$. As these regions provide sites for O-linked glycosylation, the nature of and number of these regions may account for the range of molecular weights detected on SDS-PAGE in the isolated protein. The deduced amino acid sequences for these regions are shown in FIG. 8. $ST^b$ and $ST^c$ are contained in the isoform of FIGS. 1-1 through 1-3 and 2-7 as amino acids 252–280. The cDNA and deduced amino acid sequence for $ST^a$ is also shown in FIG. 2-7, since this sequence is not contained in the isoform of these figures.

The ST-region is followed by a sequence of unknown (UK) significance, which is identical for all of the isoforms isolated. The amino acid sequence of this region is 14 amino acids in length and is shown as amino acids 281–294 of the isoform shown in FIGS. 1-1 through 1-3 and 2-1 through 2-6. The UK region is followed by a hydrophobic region (HY) which is responsible, presumably, for anchoring the MCP protein to the cellular membrane. The HY region is also identical in all of the isolated isoforms and is shown as the underlined sequence at amino acids 295–326 in FIG. 1. The HY region is followed by one of two cytoplasmic tails ($CYT^1$ or $CYT^2$). The amino acid sequence of $CYT^2$ is that shown in FIGS. 1-1 through 1-3 and 2-1 as amino acids 327–350. FIG. 2-7 also shows the cDNA and deduced amino acid sequence for $CYT^1$ The amino acid sequences of both $CYT^1$ and $CYT^2$ are shown in FIG. 8. It is seen that the $CYT^2$ encodes a 14 amino acid cytoplasmic tail, while $CYT^1$ encodes a cytoplasmic tail of 23 amino acids.

As will be demonstrated below, the human MCP isoforms of the invention can be explained by differential RNA splicing from the genomic sequence.

The MCP of the invention includes all of the foregoing isoforms, as well as their allelic variants, and as well as MCP which are encoded by DNAs capable of hybridizing under stringent conditions to the cDNAs that encode these isoforms, including those derived from other mammals. Typical stringent conditions include hybridization in 6×SSC at 65° C., followed by washing overnight at 65° C. in 0.2×SSC for an hour, or hybridization using 50% formamide in 4×SSC at 42° C., followed by washing overnight as above. Similarly, the MCP of the invention includes proteins referenced to the isoforms herein but which contain amino acid modifications while still retaining the activity of MCP as described above.

With respect to alterations, deletions and insertions of amino acids, preferred are those wherein only one, two or a small number of amino acid residues in the first 251 amino acid sequence containing the 4 SCR of the mature protein, are altered, inserted or deleted. More substantial alterations can be made downstream, as shown by the existence of a variety of MCP isoforms. Preferred substitutions are those which are conservative—i.e., hydrophobic amino acids substituted for hydrophobic amino acids, positively charged amino acids for positively charged, etc. Thus, preferred substitutions are glu for asp and vice versa, lys for his for arg and permutations thereof; substitutions among the group ile, val, met, and leu; substitutions among the group gly, ala, ser and cys; and substitutions among the group trp, tyr, and phe.

As is understood in the art, the proteins may exist in a variety of ionization states depending on the pH conditions under which they are prepared. Thus, the MCP proteins may exist in the salt form (salts formed from bases as to the carboxyl groups or acid addition salts as to the amino groups). Furthermore, the protein may be derivatized in various ways, including glycosylation, acylation, sulfation, and the like. It is believed that as glycosylation is a post-translational process, the glycosylation pattern is dependent on the nature of the cell in which the protein is produced. Differences in glycosylation pattern are particularly understood to be relevant to the present case. For example, it has been shown that the dimorphic character of the MCP extracted from membranes of various peripheral blood cells is in part accounted for by the difference in quantity of sialic acid in the two forms (Ballard, L. L., et al., *J Immunol* (1988) 141:3923–3929, incorporated herein by reference). According to this disclosure, the two forms of MCP derived from human mononuclear cells and cell lines are shown to have three of four peptides obtained by peptide mapping which are identical, whereas the largest partially digested peptide is different, and the difference in sialic residues accounts for most of the molecular weight difference between the two species.

It has been shown by the inventors herein that the difference between the 63 kd and 68 kd species as shown by SDS-PAGE is due to the presence or absence of the $ST^b$ region encoded by exon 8 of the gene. The glycosylation differences in general reflect variations at the molecular level in the splicing of the ST regions encoded by exon 7 ($ST^a$), exon 8 ($ST^b$), and exon 9 ($ST^c$).

The DNAs encoding six isoforms of human MCP are now available in the art. DNA encoding these particular embodiments can be obtained as described in the Examples below or can be synthesized de novo using known techniques. Alternatively, partial cloned sequences can be ligated to synthetic portions. Alterations in the human MCP sequences can be incorporated into the de novo synthesis or can be obtained from previously synthesized or cloned DNA using site-directed mutagenesis, as is known in the art per se. Similar isolation, modification and synthesis of other species of MCP isoforms may also be effected. Provision of and disclosure of the complete amino acid sequence for the protein acting as a cofactor, as shown in residues 1–251 of FIG. 1-1 through 1-3 or 2-1 through 2-6 permits synthesis of DNAs encoding not only this sequence, with or without the membrane-attaching and ST portions associated with it, but also alternate forms which are referenced to these proteins and to MCP proteins of other species encoded by DNA which hybridizes under the above conditions to the cDNAs encoding the human isoforms.

As to altered forms of MCP, in particular, and for illustration, TAG stop codons have been introduced into the sequence encoding the MCP isoform of FIG. 1-1 through 1-3 at the codon normally encoding serine at position 255 to obtain a shortened form of the peptide containing amino acids 1–254; in an additional embodiment, a TAG stop codon has been introduced in lieu of the codon encoding leucine at position 293 of the FIGS. 1-1 through 1-3 sequence, which immediately precedes the hydrophobic region. These solubilized forms of the protein can be produced using the recombinant techniques described below.

Production of MCP

For production of MCP using recombinant techniques, the DNA described above is preferably provided with linkers for ligation into cloning and expression vectors. Techniques for preparation of such vectors are well understood in the art. The DNA encoding the desired MCP is ligated in operable linkage with control sequences, including promoters, upstream enhancers, termination sequences, and so forth, depending on the nature of the intended recombinant host cells. Technology is currently available for expression of heterologous genes, including MCP in its various forms, in a variety of hosts, including procaryotic hosts and various eucaryotes, including yeasts, mammalian or arian or insect cells, and plant cells. The choice of control sequences and markers in the expression vectors is selected appropriately to these hosts.

For example, in procaryotic hosts, various promoters, including inducible promoters such as the trp promoter and lambda phage $P_L$ promoter can be employed. Hybrid promoters such as the tac promoter, which contains the trp polymerase binding region in combination with the lac operator, can be used. Suitable markers are generally those related to antibiotic resistance. On the other hand, in mammalian cell cultures, commonly used promoters are virally derived, such as the early and late SV40 promoters and adenovirus promoters, and the like. Some mammalian promoters are also capable of being regulated by conditions in the medium, such as the metallothionein-II promoter, which is regulated by glucocorticoids or heavy metals. These promoter systems are compatible with typical mammalian hosts, most commonly Chinese hamster ovary (CHO) cells.

Another commonly employed system is the baculovirus expression system compatible with insect cells. Plant cells, used in conjunction with, for example, the nopaline synthetase promoter, and yeast cells, used in conjunction with promoters associated with enzymes important in the glycolytic pathway, can also be employed. A number of suitable expression systems can be found in appropriate chapters in "Current Protocols in Molecular Biology," Ausubel, F. M., et al., eds., published by Wiley Interscience, latest edition.

Although greatly more laborious, the desired MCP peptide, now that its amino acid sequence has been elucidated by sequencing of the gene, could be synthesized by standard amino acid coupling techniques to obtain smaller peptides which could then be coupled using known techniques.

Regardless of the mode of preparation, whether recombinant or synthetic (or, indeed, by isolation from nature sources), the MCP is purified using techniques analogous to those described by Seya et al., *J Exp Med* (1986) 163:837.

Antibody Preparation

The purified or recombinantly produced mammalian MCP can be used to raise antibodies in suitable vertebrate subjects. Seya, T., et al., *J Exp Med* (1986) 163:837, describes the use of polyclonal antiserum to purified MCP to detect the presence or absence of MCP on various cell surfaces. In addition, the immunized mammals may be used as the source of antibody secreting cells for immortalization into cell lines capable of secreting monoclonal antibodies immunoreactive with MCP. In general, use of the standard method of Kohler and Millstein is preferred, but other methods of immortalizing cells using, for example, viral infection can also be employed. Successfully immortalized cells can be screened using standard immunoassay techniques for secretion of antibodies which bind specifically to MCP.

Utility and Administration

The purified protein is then formulated for administration using techniques known generally to treat or alleviate the symptoms of diseases and conditions characterized by excessive complement activity. Such diseases include autoimmune diseases, for example, rheumatoid arthritis, systemic lupus erythematosus, thyroiditis, myasthenia gravis, multiple sclerosis; and other diseases which are characterized by inflammation, such as arteritis of serum sickness, proteinuria in acute nephrotoxic nephritis, kidney inflammation, including glomerulitis, and insulin-dependent diabetes mellitus. In addition, the MCP of the invention may be used as a therapeutic to provide protection against tissue injury caused by disease, such as myocardial infarction, stroke, acute lung injury, and the like.

The MCP is generally formulated for injection, either systemically or directly to the tissues affected, especially body cavities such as within a joint. Suitable formulations can be found, for example, in *Remington's Pharmaceutical Sciences*, Mack Publishing Company, Easton, Pa., latest edition. For injection, the protein is dissolved or suspended in liquid medium, for example, Hank's solution, Ringer's solution, dextrose solution, and various buffers. Additional excipients such as stabilizers can also be employed.

Besides injection, the peptides of the invention can be administered systemically, via suppository, oral administration, transmucosal administration, including intranasal sprays, and by slow release formulations. Additional formulation techniques include encapsulation formulations, such as liposomes.

Finally, the peptides of the invention can be conjugated to target-directing ligands to carry them to the site of desired bioactivity. Such ligands can include, most commonly, immunoglobulins or their fragments and ligands specific for cell-associated receptors. Targeted forms of the MCP are particularly useful in treating allograft rejections by targeting the foreign tissue.

In addition to utility as a therapeutic, the MCP isoforms can be used individually to raise polyclonal antisera or to produce cells which can be fused to immortalizing partners to obtain sources of monoclonal antibodies specific for these isoforms of MCP. These antibodies are useful as a passive therapeutic to treat diseases which are characterized by low complement activity, or to remedy deficiencies in the complement system, and also to raise antiidiotypic antibodies which are, in turn, therapeutically useful. The antibodies are also useful diagnostic tools for assay of MCP levels on peripheral blood cells or other normally MCP-bearing cells using standard immunoassay techniques.

The cDNA of the invention, homologous to that shown in FIGS. 1-1 through 2-1 through 2-6 or 3 is also useful as a probe to recover analogous MCP-encoding DNAs in a variety of species, in addition to human. This cDNA or its homologs can be used diagnostically as a probe to measure levels of MCP in placental tissue; these levels may be predictive of propensity for miscarriages in future pregnancies.

The following examples are intended to illustrate but not limit the invention.

EXAMPLE 1

Preparation of Purified Human MCP

The procedure of Seya, T., et al., *J Exp Med* (1986) 163:837, cited above, and incorporated herein by reference was employed. The protein was purified from the T cell line HSB2 by solubilization in NP-40 followed by sequential chromatography on chromatofocusing, hydroxyapatite, C3 (methylamine) Sepharose, and Mono Q columns. Approximately 20 ug of partially purified protein thus obtained was subjected to 10% SDS-PAGE and the 63 kd $M_r$ band was electroeluted and electrodialyzed according to the procedure of Hunkapiller, M. W., et al., *Meth Enzymol* (1983) 91:227. The resulting protein was homogeneous according to the criteria of SDS-PAGE and HPLC.

EXAMPLE 2

Recovery of cDNA-encoding MCP

The monocyte U937 cell line was used as a source of mRNA. This was prepared using standard procedures including guanidinium isothiocyanate/CsCl extraction as described by Chirgwin, J. M., et al., *Biochemistry* (1979) 18:5294, followed by isolation of mRNA on oligo(dT)cellulose chromatography (Aviv, H., et al., *Proc Natl Acad Sci USA* (1972) 69:1408. The cDNA library was prepared from 5 ug of the isolated mRNA by the method of Gubler, U., et al., Gene (1983) 25:263 and cDNA inserts of greater than 1 kb were ligated into lambda-gt10 arms, packaged and plated on C600 hflA *E. coli* to obtain $2\times10^6$ recombinants. The cDNA library was probed with a $^{32}$P-labeled 64 degenerate 17-mer antisense oligonucleotide probe based on residues 7–12 of the MCP protein as determined by amino acid sequencing of the purified protein of Example 1. The 17-mer encoded the sequence Phe-Glu-Ala-Met-Glu-Leu. The library was probed on plaque lifts on nitrocellulose filters wherein the filters the filters were hybridized overnight at 37° C. in 6×SSC (1×SSC–0.15M sodium chloride/0.015M sodium citrate)/5×Denhardt's solution (1×Denhardt's= 0.02% BSA/0.02% Ficoll/0.02% polyvinyl-pyrrolidone)/ 0.05M sodium phosphate, pH 6.8, containing 100 ug sonicated herring sperm DNA and $5\times10^5$ cpm labeled probe per ml. The filters were washed two times for 30 min with 2×SSC/0.1% SDS at room temperature.

The plaques yielding positive signals in duplicate were plaque purified using standard methods.

The positive plaques were cloned into pUC-19 and sequenced using the standard dideoxy sequencing method. One clone which contained a 1.5 kb insert was sequenced with the results shown in FIGS. 1-1 through 1-3.

As shown in FIGS. 1-1 through 1-3, the cDNA contains an open reading frame encoding 384 amino acids. The first 34 amino acids are a typical structure for a signal peptide; the succeeding 24 amino acids match the N-terminal protein sequence determined by Edman degradation of the protein in Example 1. The putative protein without signal of 39 kd agrees with the size of-the MCP precursor detected in biosynthetic studies by Ballard, L. L., et al., *J Immunol (*1988) 141:3923–3929. It will be seen that there are 3 N-linked glycosylation sites and multiple potential O-linked glycosylation sites in the ser/thr-rich region (12/25 residues) between amino acids 253–277, consistent with the oligosaccharide structure of MCP as determined by Ballard et al., supra. Hydrophobicity analysis according to Hopp, T. P., et al., *Proc Natl. Acad Sci USA (*1981) 78:3824 show a 23-amino acid region typical for a transmembrane hydrophobic domain at amino acids 295–317, followed by a 33-amino acid region corresponding to a cytoplasmic tail. The untranslated downstream region is consistent with a polyadenylation site.

However, the bulk of the protein at the N-terminus consists of 4 contiguous domains of about 60 amino acids which match the consensus sequence found in the multigene family of complement regulatory proteins. These 4 domains show 18–35% amino acid sequence homology to each other (29–44% if conservative amino acid sequences are allowed) similar to the degree of homology in other members of the family.

EXAMPLE 3

Preparation of cDNAs for Alternate Isoforms

A cDNA library of human skin fibroblasts in lambda-gt10 from Clonetech Laboratories (Palo Alto, Calif.) was used as one source for cDNA encoding MCP. A second library was prepared from 10 ug HeLa poly $A^+$ RNA, obtained from Clonetech by segregating cDNA inserts of greater than 3 kb by agarose gel electrophoresis and ligating these inserts into lambda ZAP$^R$II packaged in a Gigapack™ and plated on XL1-Blue *E. coli* (all from Stratagene, La Jolla, Calif.). The libraries were probed with the cDNA of FIGS. 1-1 through 1-3 labeled by random hexanucleotide priming. Positive clones were plaque purified and isolated using a small scale bacteriophage preparation as described by Ausubel, F. M., et al., *Current Protocols in Molecular Biology* (1987) John Wiley & Sons, Inc., p. 1. The inserted DNA was then subcloned into the EcoRI site of pUC19 as described by Maniatis, T., et al., *Molecular Cloninq: A Laboratory Manual* (1982) Cold Spring Harbor Laboratory, Cold Spring Harbor, NY.

Another cDNA encoding the isoform of FIGS. 1-1 through 1-3, but having extended untranslated regions is shown in FIGS. 2-1 through 2-6. This cDNA was retrieved in this manner from the skin fibroblast library as a 3.2 kb clone. This clone contains an additional 102 nucleotides of 5' untranslated sequence and an additional 1582 nucleotides of 3' untranslated sequence. The encoded protein is identical to that of FIGS. 1-1 through 1-3.

A second MCP isoform was obtained by screening the HeLa cDNA library with the cDNA of FIGS. 1-1 through 1-3 labeled as described above. The translated region of this clone, designated H-27 in FIG. 3, differs in that it contains a 93 nucleotide insert that includes a stop codon located immediately after the hydrophobic region. This insert results in a different cytoplasmic tail ($CYT^1$) of only 16 amino acids, rather than the 23 amino acid $CYT^2$ shown in FIGS. 1-1 through 1-3 and 2-6. The DNA encoding the $CYT^2$ cytoplasmic tail of FIGS. 1 and 2-1 is included in the untranslated sequence in the mRNA encoding this isoform.

Figures 9A, 9B:
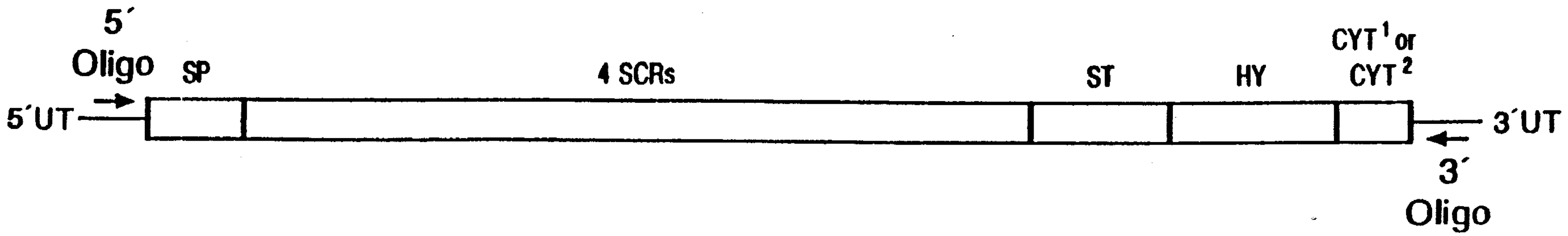
FIGS. 9A and 9B show the primers used for PCR synthesis of the DNA encoding the MCP isoforms.

In order to obtain additional isoforms, MCP-specific primers from the 5' and 3' untranslated regions of MCP cDNA of FIG. 1 were used to produce clones which span the coding region of MCP using the polymerase chain reaction (PCR). The sequences of the primers, which contain convenient restriction sites, are shown in FIGS. 9A and 9B. The PCR products prepared from total RNA of the erythroleukemia cell line K-562 and the hepatoma cell line HEp-2 were ethanol precipitated, digested with EcoRI, gel purified and subcloned into the EcoRI site of pUC19, and then characterized by size and by digestion with SalI. Distinct subclones were then sequenced.

The results of this sequencing showed the availability of the six isoforms shown in FIG. 3, which diagrams the mapping of the cDNA for these retrieved sequences in comparison to that obtained from U937 cells and skin fibroblast cells shown in FIGS. 1-1 through 1-3 and 2-1 through 2-6. The resulting 6 isoforms differ only in the nature of the ST and CYT regions.

EXAMPLE 4

Organization of the MCP Gene

Figure 4:
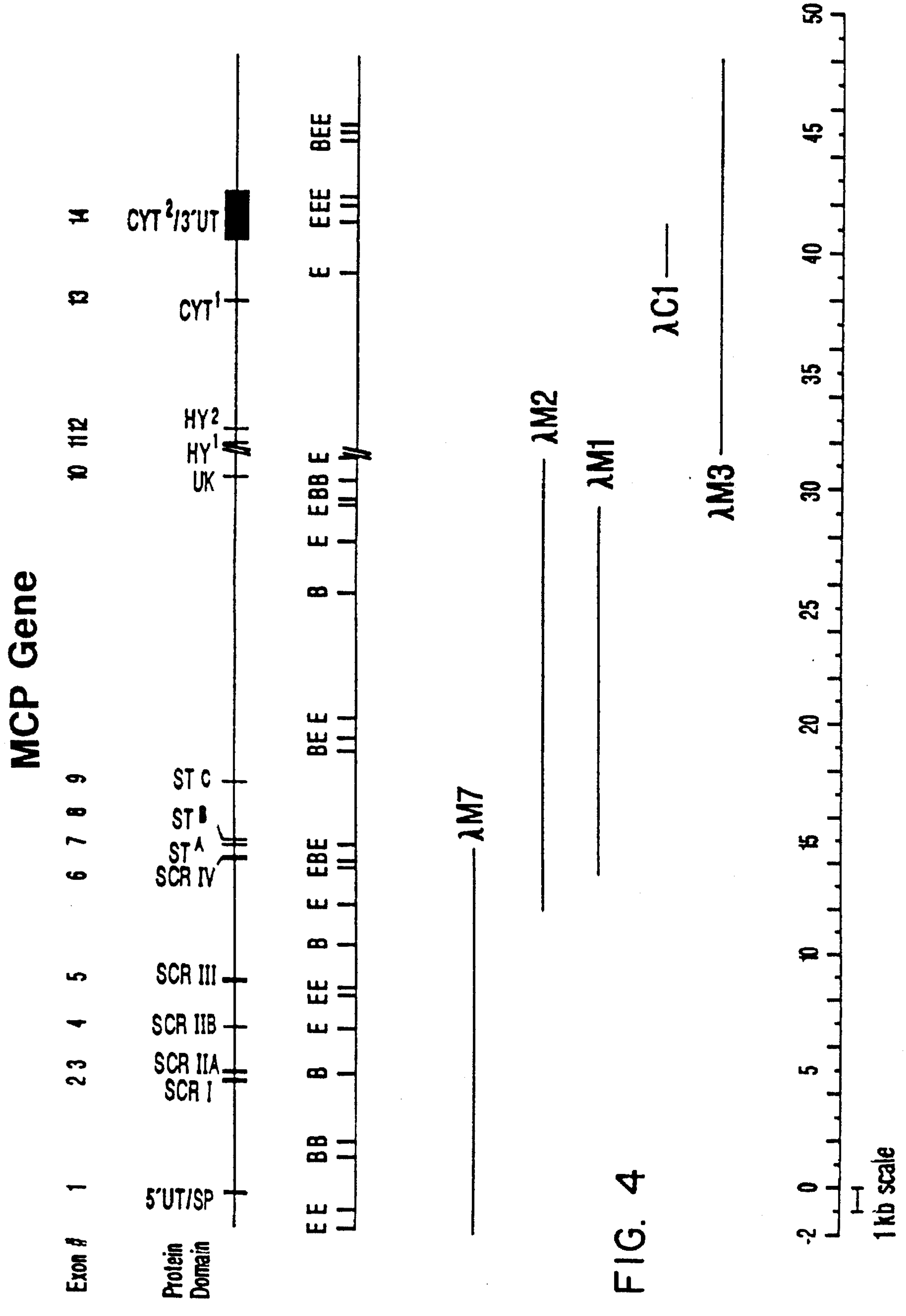
Figure 6:
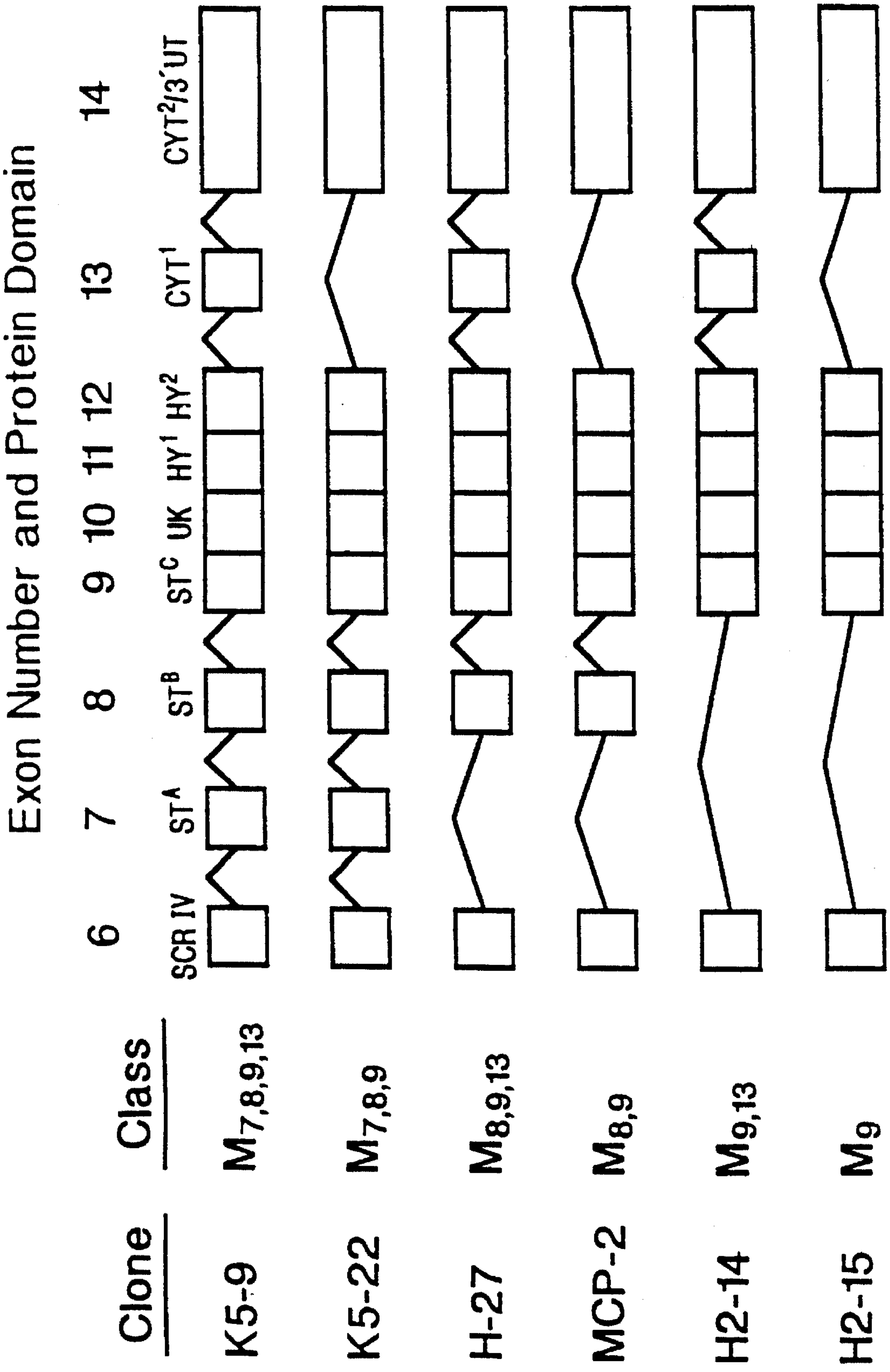

Southern blots of total genomic DNA digested with EcoRI and BamHI were probed with the cDNA clone of FIG. 1 labeled as described above and resulted in a complex pattern of labeled fragments. To retrieve the appropriate sequence, 3 genomic libraries were probed: an EcoRI library cloned into Charon-4A from the American-Type Culture Collection, a Sau3AI library cloned into lambda DASH obtained from Stratagene Cloning Systems, and a chromosome-1 specific library obtained from ATCC constructed by EcoRI digestion and insertion into Charon-21A. Screening of these libraries as described resulted in 5 genomic bacteriophage clones which contained 14 exons spread over a length of approximately 43 kb which, however, do not completely overlap. As shown in FIG. 4, the MCP gene consists of 14 exons and 13 introns. The exon sequences exactly matched those obtained for MCP cDNA and PCR clones. All exon/intron boundaries conform to the GT/AG consensus sequence rule as shown in FIG. 5. A map of the gene and a diagram of the splicing which results in the six disclosed isoforms is shown in FIG. 6.

The first exon encodes the 5' untranslated/signal peptide region, although the length of this exon is not known since the transcription start site has not been determined. The next 5 exons encode the 4 SCR repeats. Each of SCRs 1, 3 and 4 are encoded by a single exon while Exon 2 is encodes by 2 exon. Exon 7 encodes $ST^a$, exon 8 encodes $ST^b$, and exon 9 encodes $ST^c$. It appears that the different isoforms are determined by which of the transcribed exons are spliced into the resulting mRNA as shown.

Exon 10 encodes the 13 amino acid stretch of unknown significance (UK) common to all isoforms, and exons 11 and 12 encode the hydrophobic transmembrane domain and basic amino acid anchor.

Exon 13 encodes the 93 nucleotide stretch encoding $CYT^1$ which, when included, terminates the cytoplasmic tail after 16 amino acids. When this transcribed exon is missing from the RNA, the presence of exon 14 results in an in-frame reading of the $CYT^2$23 amino acid cytoplasmic tail.

EXAMPLE 5

Production of Recombinant MCPs

The cDNA encoding MCP-1, H2–15, H2–14, and K5–23 (H-27) (see FIG. 3), as well as the cDNA of FIGS. 1-1 through 1-3 with stop codons inserted at positions 255 or 293, was ligated into an expression vector suitable for recombinant production of the protein in COS and CHO cells. Significant amounts of these recombinant proteins were produced both in the transient system of COS cells and the stable expression system contained in CHO cells.

For expression of high amounts of both membrane-bound and -secreted MCP, appropriate cDNAs are cloned into the pSVL SV40 late expression vector under the control of SV40 late promoter. MCP cloned into pSVL vector is then cotransfected with pSV3-dhfr carrying dihydrofolate reductase (dhfr) gene into a dhfr-mutant CHO cell line. As a result of cotransfection, dhfr+ clones making MCP are produced. High producers of MCP are then selected by incubation in the presence of increasing concentrations of methotrexate.

For analysis of individual isoforms, the cDNA for each is placed in pSFFV.neo or pHbetaApr1.neo. The vector containing the cDNA is then transfected into COS cells to produce transient lines or into CHO or NIH-3T3 cells to produce permanent cell lines. Permanent cell lines have been produced for the six major isoforms of MCP, and FACS has been used to select for high producers.

EXAMPLE 6

Monoclonal Antibodies as Reagents

Three mouse monoclonal antibodies, designated E4.3, GB-24 and TRA-10, were prepared to human MCP. All bind to MCP by FACS analysis and immunoprecipitation, and have been purified, labeled with I-125, and studied with respect to epitope mapping of MCP.

TRA2-10 inhibits the binding of E4.3 and also displaces E4.3 from its epitope on MCP, showing that both bind to the same epitope and that TRA2-10 has a higher affinity. These antibodies do not compete with GB-24.

GB-24 inhibits the cofactor activity of MCP, while E4.3 and TRA2-10 do not.

The foregoing monoclonal antibodies are also used in direct binding studies to quantitate the number of copies of MCP on cell lines and in human peripheral blood cells. For example, one assay utilizes TRA2-10 coated onto plastic wells, a sample to be tested for MCP is added, and after washing, 125-iodinated GB-24 is added. In an alternate assay, the cells are incubated with human/mouse Ig and then with labeled TRA2-10; using this assay, the results shown in Table 1, assessing the number of copies of MCP/cell in various human peripheral blood cells and cell lines, were obtained.

TABLE 1

| Number of Copies of MCP/Cell[a] | |
|---|---|
| Human Peripheral Blood Cells[b] | |
| Erythrocytes | Negative |
| Platelets | 300 to 400 |

TABLE 1-continued

| Number of Copies of MCP/Cell[a] | | |
|---|---|---|
| Human Peripheral Blood Cells[b] | | |
| Granulocytes | 10,000 to 12,000 | |
| Mononuclear | 8,000 to 10,000 | |
| Human Cell Lines[c] | | |
| K562 | 76,000 | erythrocytic leukemia |
| U937 | 92,000 | monocyte-like |
| HeLa | 100,000 | epithelial |
| Hep-2 | 250,000 | epithelial |
| HL-60 | 64,000 | promyelocytic leukemia |
| Daudi | 12,000 | B-lymphocyte |
| Molt 4 | 12,000 | T-lymphocyte |
| Raji | 7,000 | B-lymphocyte |
| SKW | 25,000 | B-lymphocyte |
| EB-19 | 38,000 | EB virus transformed B lymphocyte |
| EB-22 | 17,000 | EB virus transformed B lymphocyte |
| EB-16/19 | 29,000 | EB virus transformed B lymphocyte |
| EB-19/16 | 27,000 | EB virus transformed B lymphocyte |
| EB-19/22 | 33,000 | EB virus transformed B lymphocyte |
| EB-19/25 | 33,000 | EB virus transformed B lymphocyte |

[a]Purified human peripheral blood cell populations (mononuclear cells, erythrocytes, granulocytes, platelets) or human cell lines are incubated with human/mouse IgG for 30 min at 4° C. and then for 1 hr at 4° C. with purified $^{125}$I-labeled monoclonal anti-MCP (for these experiments TRA2-10 was utilized).
[b]These data represent the range of two normal individuals performed on two separate occasions.
[c]Mean of at least two separate determinations.

I claim:

1. An insolated soluble mammalian membrane cofactor protein which inhibits complement, has cofactor activity, and is free of decay-accelerating activity, said membrane cofactor protein lacking the membrane-bound region of native membrane cofactor protein.

2. The isolated membrane cofactor protein of claim 1 which is recombinantly produced in genetically engineered cells.

3. The isolated membrane cofactor protein of claim 1 which consists essentially of the amino acid sequence shown as amino acids 1–251 of FIGS. 1-1 through 1-3.

4. The isolated membrane cofactor protein of claim 1 which consists essentially of the amino acid sequence shown as amino acids 1–293 of FIGS. 1-1 through 1-3.

5. The isolated membrane cofactor protein of claim 3 which contains 1 or 2 amino acid conservative substitutions from the amino acid sequence shown as amino acids 1–251 of FIGS. 1-1 through 1-3.

6. The isolated membrane cofactor protein of claim 4 which contains 1 or 2 amino acid conservative substitutions from the amino acid sequence shown as amino acids 1–293 of FIGS. 1-1 through 1-3.

7. The isolated membrane cofactor protein of claim 1 wherein the sequence is the amino acid sequence from residues 1 to 251 of FIGS. 1-1 through 1-3.

8. The isolated membrane cofactor protein of claim 1 wherein the sequence is the amino acid sequence from residues 1 to 293 of FIGS. 1-1 through 1-3.

9. The isolated membrane cofactor protein of claim 1 which is encoded by a DNA which hybridizes under stringent conditions to the complement of the DNA encoding amino acids 1–251 of FIGS. 1-1 through 1-3 or FIGS. 2-1 through 2-6 and is lacking a membrane binding region.

10. The isolated membrane cofactor protein of claim 9 which contains 1 or 2 amino acid conservative substitutions of the amino acid sequence shown as amino acids 1–251 of FIGS. 1-1 through 1-3.

11. A pharmaceutical composition useful for inhibiting complement activity, which comprises the membrane cofactor protein of claim 1 as active ingredient in admixture with a suitable excipient.

12. A pharmaceutical composition useful for inhibiting complement activity, which comprises the membrane cofactor protein of claim 2 as active ingredient in admixture with a suitable excipient.

13. A method to inhibit complement activity, in a subject, which method comprises administering to a subject in need of such treatment an effective amount of the membrane cofactor protein of claim 1, or a pharmaceutical composition thereof, to inhibit complement activity.

14. A method to inhibit complement activity in a subject, which method comprises administering to a subject in need of such treatment an effective amount of the membrane cofactor protein of claim 2 or pharmaceutical composition thereof to inhibit complement activity.

* * * * *